US009895419B2

(12) United States Patent
Yates-Binder et al.

(10) Patent No.: US 9,895,419 B2
(45) Date of Patent: Feb. 20, 2018

(54) GOBLET CELL REPLACEMENT THERAPY

(71) Applicant: University of Pittsburgh—Of the Commonwealth System of Higher Education, Pittsburgh, PA (US)

(72) Inventors: Cecelia C. Yates-Binder, Pittsburgh, PA (US); Alan H. Wells, Pittsburgh, PA (US); Joel S. Schuman, Pittsburgh, PA (US); Ian P. Conner, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/113,035

(22) PCT Filed: Jan. 20, 2015

(86) PCT No.: PCT/US2015/012062
§ 371 (c)(1),
(2) Date: Jul. 20, 2016

(87) PCT Pub. No.: WO2015/112505
PCT Pub. Date: Jul. 30, 2015

(65) Prior Publication Data
US 2017/0000852 A1    Jan. 5, 2017

Related U.S. Application Data

(60) Provisional application No. 61/929,654, filed on Jan. 21, 2014.

(51) Int. Cl.
*A61K 38/19* (2006.01)
*A61K 9/00* (2006.01)
*A61K 47/48* (2006.01)

(52) U.S. Cl.
CPC .......... *A61K 38/195* (2013.01); *A61K 9/0048* (2013.01); *A61K 38/19* (2013.01); *A61K 47/4823* (2013.01); *A61K 47/48215* (2013.01)

(58) Field of Classification Search
None
See application file for complete search history.

(56) References Cited

U.S. PATENT DOCUMENTS

| | | | |
|---|---|---|---|
| 5,994,292 A | 11/1999 | Tosato et al. | |
| 8,734,775 B2 * | 5/2014 | Yates-Binder | A61K 38/195 424/85.2 |
| 2005/0208496 A1 | 9/2005 | Ohtani et al. | |
| 2007/0087001 A1 | 4/2007 | Taylor et al. | |
| 2013/0053319 A1 | 2/2013 | Yates-Binder et al. | |
| 2014/0178451 A1 | 6/2014 | Wells et al. | |

FOREIGN PATENT DOCUMENTS

| | | |
|---|---|---|
| EP | 2 287 183 | 2/2011 |
| WO | WO 2005/113597 | 12/2005 |
| WO | WO 2007/033215 | 3/2007 |
| WO | WO 2007/149542 | 12/2007 |
| WO | WO 2013/032853 | 3/2013 |

OTHER PUBLICATIONS

Olmos et al. "Medical and Surgical Treatment of Neovascular Glaucoma," Published in final edited form as: Int Ophthalmol Clin. 2011 ; 51(3): 27-36, Author Manuscript available in PMC Jul. 1, 2012, pp. 1-10.*
Abu El-Asrar et al., "The T-lymphocyte Chemoattractant Mig is Highly Expressed in Vernal Keratoconjunctivitis," *Am. J. Opthalmol.*, vol. 136:853-860, 2003.
Addison et al., "The CXC Chemokine Receptor 2, CXCR2, Is the Putative Receptor for ELR+ CXC Chemokine-Induced Angiogenic Activity," *J. Immunol.*, 165:5269-5277, 2000.
Berendsen, "A Glimpse of the Holy Grail?" *Science*, vol. 282:642-643, 1998.
Bodnar et al., "IP-10 Blocks Vascular Endothelial Growth Factor-Induced Endothelial Cell Motility and Tube Formation via Inhibition of Calpain," *Circ Res* 98:617-625, 2006.
Bodnar et al., "IP-10 induces dissociation of newly formed blood vessels," *J Cell Sci.*, 122:2064-2077, 2009.
Bradley et al., "Limits of Cooperativity in a Structurally Modular Protein: Response of the Notch Ankyrin Domain to Analogous Alanine Substitutions in Each Repeat," *J. Mol. Biol.*, vol. 324:373-386, 2002.
Campanella et al., "CXCR3 and Heparin Binding Sites of the Chemokine IP-10 (CXCL10)," *J. Biol. Chem.*, vol. 278:17066-17074, 2003.
Coursey et al., "Chemokine Receptors CCR6 and CXCR3 are Necessary for CD4+ T Cell Mediated Ocular Surface Disease in Experimental Dry Eye Disease," *PLoS One*, vol. 8:e78508, 2013.
Ingrams, et al., "Sinus Surgery: Does Mitomycin C Reduce Stenosis?" *Laryngoscope*, vol. 108:883-886, 1998.
Lee et al., "Intravitreal Bevacizumab (Avastin) Treatment of Neovascular Glaucoma in Ocular Ischemic Syndrome," *Korean J. Opthalmol.*, vol. 23:132-134, 2009.
Mabeta et al., "A Comparative Study on the Anti-Angiogenic Effects of DNA-Damaging and Cytoskeletal-Disrupting Agents," *Angiogenesis*, vol. 12:81-90, 2009.
Mehvar, "Dextrans for Targeted and Sustained Delivery of Therapeutic and Imaging Agents," *J. Control. Rel.*, vol. 69:1-25, 2000.
Ngo et al., "Computational Complexity, Protein Structure Prediction, and the Levinthal Paradox," The Protein Folding Problem and Tertiary Structure Prediction, pp. 491-494, 1994.
Rudinger, "Characteristics of the Amino Acids as Components of a Peptide Hormone Sequence," *Peptide Hormones*, University Park Press, Baltimore, pp. 1-7, 1976.

(Continued)

*Primary Examiner* — Christina Bradley
(74) *Attorney, Agent, or Firm* — Klarquist Sparkman, LLP

(57) ABSTRACT

Described herein is the finding that activators of CXCR3, such as proteins that bind CXCR3 (e.g., IP-9, IP-10 and PF4), enhance the density of goblet cells in the eye. Goblet cells in the conjunctiva are the primary source of tear mucus. Accordingly, the present disclosure describes methods of treating dry eye syndrome by administering an activator of CXCR3. Also described are methods of increasing goblet cells density, such as goblet cell density in the conjunctiva.

20 Claims, 5 Drawing Sheets

(56) References Cited

OTHER PUBLICATIONS

Sigma Genosys, "Designing Custom Peptides," www.sigma-genosys.com/peptide_design.asp, downloaded Dec. 16, 2004, 2 pages.

Stroke et al., "Identification of CXCR3 Receptor Agonists in Combinatorial Small-Molecule Libraries," *Biochem. Biophys. Res. Comm.*, vol. 349:221-228, 2006.

Voet, "Hemoglobin: Protein Function in Microcosm", *Biochemistry*, Second Ed., John Wiley & Sons, Inc., New York, pp. 235-241, 1995.

Yates-Binder et al., "An IP-10 (CXCL10)-Derived Peptide Inhibits Angiogenesis," *PLoS One* 7:e40812, 2012.

Yoon et al., "Expression of CXCL9, -10, -11, and CXCR3 in the Tear Film and Ocular Surface of Patients with Dry Eye Syndrome," *Invest. Ophthalmol. Vis. Sci.*, vol. 51:643-650, 2010.

* cited by examiner

FIG. 1

Histologic Differences in Treated Blebs

| | Uninjured | Control | P.10L | P.10P |
|---|---|---|---|---|
| Inflammation | -- | +++ | ++ | + |
| Elastic Fibers (Thickness) | + / -- | +++ | + | + |
| Fibrosis | -- | +++++ | + | ++ |

-- = absent; + / -- = weakly present; +, ++, +++, ++++, +++++ = present in increasing amounts, graded by masked observer

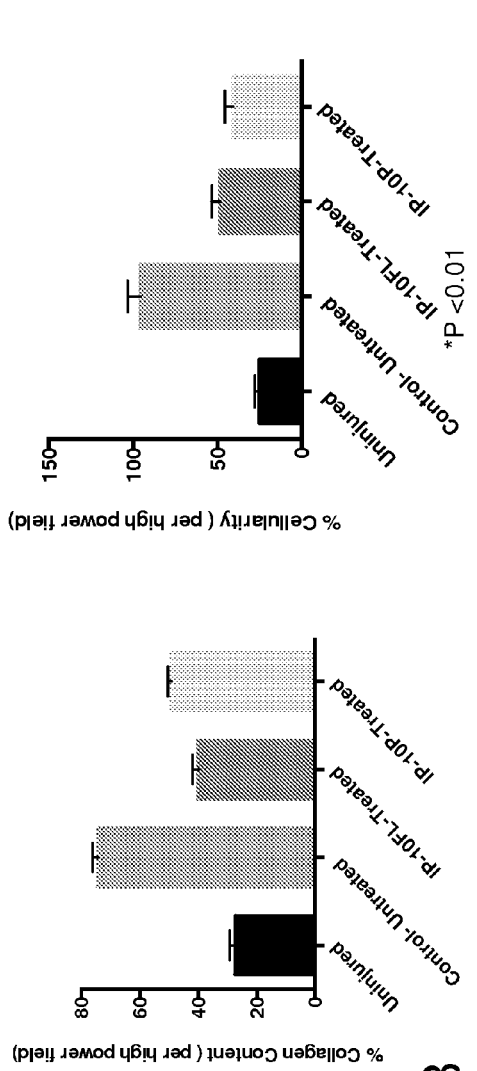
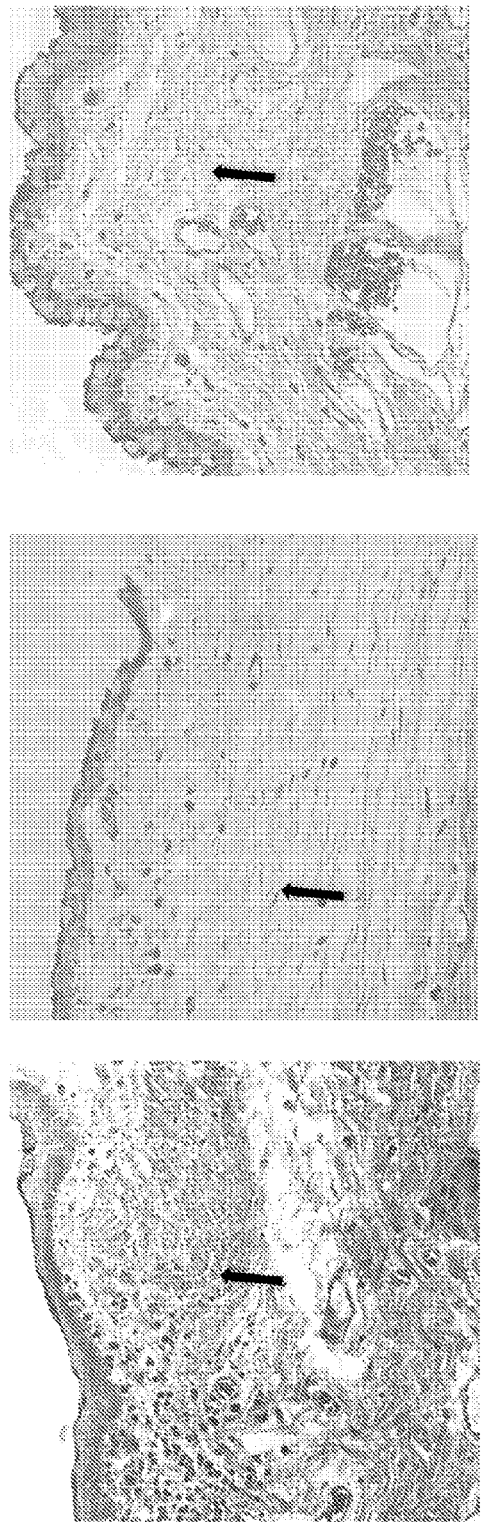
FIG. 3A
FIG. 3B

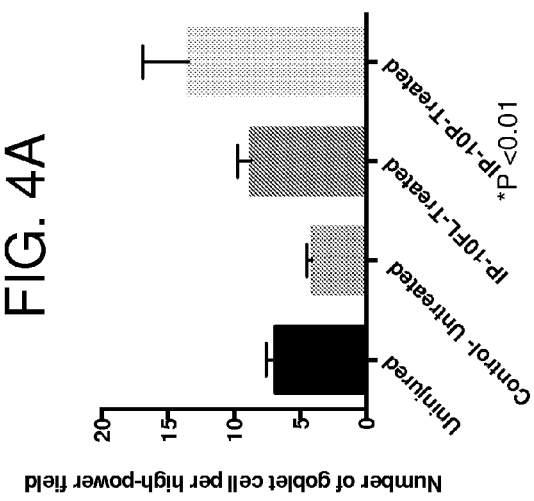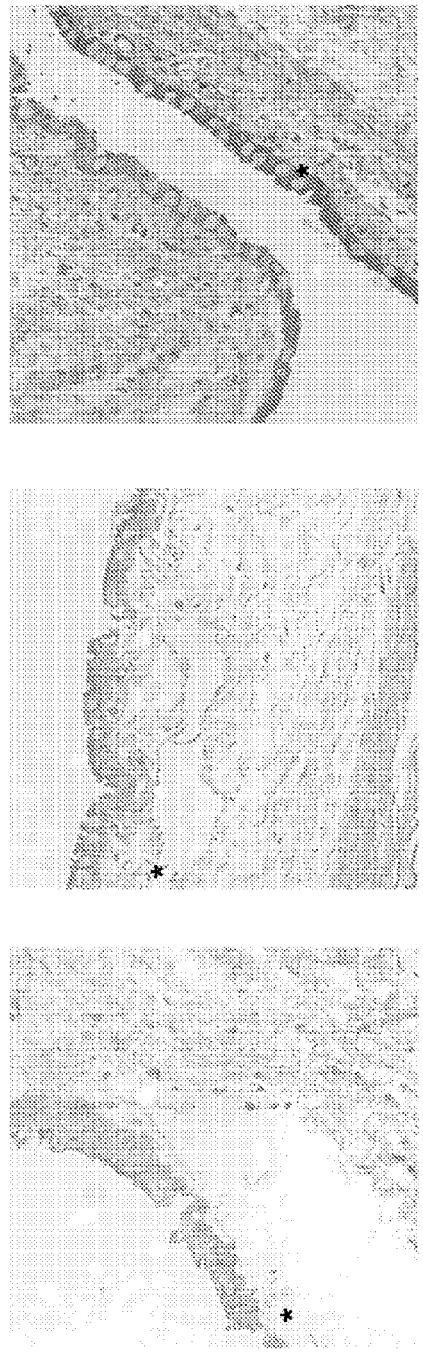

MMC-Treated  MMC/IP-10P-Treated

SEQUENCE LISTING

```
<160> NUMBER OF SEQ ID NOS: 14

<210> SEQ ID NO 1
<211> LENGTH: 98
<212> TYPE: PRT
<213> ORGANISM: Homo sapiens

<400> SEQUENCE: 1

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro
```

-continued

<210> SEQ ID NO 2
<211> LENGTH: 21
<212> TYPE: PRT
<213> ORGANISM: Homo sapiens

<400> SEQUENCE: 2

Glu Ser Lys Ala Ile Lys Asn Leu Leu Lys Ala Val Ser Lys Glu Arg
1               5                   10                  15

Ser Lys Arg Ser Pro
            20

<210> SEQ ID NO 3
<211> LENGTH: 70
<212> TYPE: PRT
<213> ORGANISM: Homo sapiens

<400> SEQUENCE: 3

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 4
<211> LENGTH: 29
<212> TYPE: PRT
<213> ORGANISM: Homo sapiens

<400> SEQUENCE: 4

Asp Leu Gln Cys Leu Cys Val Lys Thr Thr Ser Gln Val Arg Pro Arg
1               5                   10                  15

His Ile Thr Ser Leu Glu Val Ile Lys Ala Gly Pro His
                20                  25

<210> SEQ ID NO 5
<211> LENGTH: 22
<212> TYPE: PRT
<213> ORGANISM: Homo sapiens

<400> SEQUENCE: 5

Pro Glu Ser Lys Ala Ile Lys Asn Leu Leu Lys Ala Val Ser Lys Glu
1               5                   10                  15

Arg Ser Lys Arg Ser Pro
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic polypeptide

<400> SEQUENCE: 6

Glu Ser Lys Ala Ile Lys Asn Leu Leu Lys Ala Val Ser Lys Glu Met
1               5                   10                  15

Ser Lys Arg Ser Pro
            20

<210> SEQ ID NO 7
<211> LENGTH: 98
<212> TYPE: PRT
<213> ORGANISM: Mus musculus

<400> SEQUENCE: 7

Met Asn Pro Ser Ala Ala Val Ile Phe Cys Leu Ile Leu Leu Gly Leu
1               5                   10                  15

Ser Gly Thr Gln Gly Ile Pro Leu Ala Arg Thr Val Arg Cys Asn Cys
            20                  25                  30

Ile His Ile Asp Asp Gly Pro Val Arg Met Arg Ala Ile Gly Lys Leu
        35                  40                  45

Glu Ile Ile Pro Ala Ser Leu Ser Cys Pro Arg Val Glu Ile Ile Ala
    50                  55                  60

Thr Met Lys Lys Asn Asp Glu Gln Arg Cys Leu Asn Pro Glu Ser Lys
65                  70                  75                  80

Thr Ile Lys Asn Leu Met Lys Ala Phe Ser Gln Lys Arg Ser Lys Arg
                85                  90                  95

Ala Pro

<210> SEQ ID NO 8
<211> LENGTH: 21
<212> TYPE: PRT
<213> ORGANISM: Mus musculus

<400> SEQUENCE: 8

Glu Ser Lys Thr Ile Lys Asn Leu Met Lys Ala Phe Ser Gln Lys Arg
1               5                   10                  15

Ser Lys Arg Ala Pro
            20

<210> SEQ ID NO 9
<211> LENGTH: 22
<212> TYPE: PRT
<213> ORGANISM: Mus musculus

<400> SEQUENCE: 9

Pro Glu Ser Lys Thr Ile Lys Asn Leu Met Lys Ala Phe Ser Gln Lys
1               5                   10                  15

Arg Ser Lys Arg Ala Pro
            20

<210> SEQ ID NO 10
<211> LENGTH: 13
<212> TYPE: PRT
<213> ORGANISM: Homo sapiens

<400> SEQUENCE: 10

Pro Leu Tyr Lys Lys Ile Ile Lys Lys Leu Leu Glu Ser
1               5                   10

<210> SEQ ID NO 11
<211> LENGTH: 18
<212> TYPE: PRT
<213> ORGANISM: Homo sapiens

<400> SEQUENCE: 11

Leu Asp Leu Gln Ala Pro Leu Tyr Lys Lys Ile Ile Lys Lys Leu Leu
1               5                   10                  15

Glu Ser

<210> SEQ ID NO 12
<211> LENGTH: 77
<212> TYPE: PRT
<213> ORGANISM: Artificial Sequence
<220> FEATURE:
<223> OTHER INFORMATION: Synthetic polypeptide

<400> SEQUENCE: 12

```
Val Pro Leu Ser Arg Thr Val Arg Cys Thr Cys Ile Ser Ile Ser Asn
1               5                   10                  15

Gln Pro Val Asn Pro Arg Ser Leu Glu Lys Leu Glu Ile Ile Pro Ala
            20                  25                  30

Ser Gln Phe Ser Pro Arg Val Glu Ile Ile Ala Thr Met Lys Lys Lys
        35                  40                  45

Gly Glu Lys Arg Cys Leu Asn Pro Glu Ser Lys Ala Ile Lys Asn Leu
    50                  55                  60

Leu Lys Ala Val Ser Lys Glu Met Ser Lys Arg Ser Pro
65                  70                  75
```

<210> SEQ ID NO 13
<211> LENGTH: 22
<212> TYPE: PRT
<213> ORGANISM: Artificial Sequence
<220> FEATURE:
<223> OTHER INFORMATION: Synthetic polypeptide

<400> SEQUENCE: 13

```
Pro Glu Ser Lys Ala Ile Lys Asn Leu Leu Lys Ala Val Ser Lys Glu
1               5                   10                  15

Met Ser Lys Arg Ser Pro
            20
```

<210> SEQ ID NO 14
<211> LENGTH: 94
<212> TYPE: PRT
<213> ORGANISM: Homo sapiens

<400> SEQUENCE: 14

```
Met Ser Val Lys Gly Met Ala Ile Ala Leu Ala Val Ile Leu Cys Ala
1               5                   10                  15

Thr Val Val Gln Gly Phe Pro Met Phe Lys Arg Gly Arg Cys Leu Cys
            20                  25                  30

Ile Gly Pro Gly Val Lys Ala Val Lys Val Ala Asp Ile Glu Lys Ala
        35                  40                  45

Ser Ile Met Tyr Pro Ser Asn Asn Cys Asp Lys Ile Glu Val Ile Ile
    50                  55                  60

Thr Leu Lys Glu Asn Lys Gly Gln Arg Cys Leu Asn Pro Lys Ser Lys
65                  70                  75                  80

Gln Ala Arg Leu Ile Ile Lys Lys Val Glu Arg Lys Asn Phe
            85                  90
```

GOBLET CELL REPLACEMENT THERAPY

CROSS REFERENCE TO RELATED APPLICATIONS

This is the U.S. National Stage of International Application No. PCT/US2015/012062, which claims the benefit of U.S. Provisional Application No. 61/929,654, filed Jan. 21, 2014, which is herein incorporated by reference in its entirety.

FIELD

This disclosure concerns the use of activators of CXCR3 to increase the density of goblet cells in epithelial tissue and/or to treat dry eye syndrome.

BACKGROUND

Dry eye syndrome, also known as keratoconjunctivitis sicca, is a multifactorial disorder of the tears and ocular surface that results in symptoms of discomfort, visual disturbance, and tear film instability. Dry eye syndrome is usually caused by inadequate tear production. In such cases, the lacrimal gland does not produce sufficient tears to keep the entire conjunctiva and cornea covered by a complete layer. This typically occurs in people who are otherwise healthy; however, increased age is associated with decreased tearing.

Dry eye syndrome can also be caused by abnormal tear composition resulting in rapid evaporation or premature destruction of the tears. In this condition, although the tear gland produces a sufficient amount of tears, the rate of evaporation of the tears is too rapid. There is a loss of water from the tears that results in tears that are hypertonic. As a result, the entire conjunctiva and cornea cannot be kept covered with a complete layer of tears during certain activities or in certain environments.

Goblet cells are polarized epithelial cells found in columnar and stratified squamous epithelia throughout the body, such as in the conjunctiva. Goblet cells secrete gel-forming mucins that form the mucous layer that protects the wet-surfaced epithelia from the external environment. These cells form the first line of defense between the ocular surface, the inner ear, the gastrointestinal tract and the respiratory tract with the external environment. Goblet cells of the conjunctiva are the primary source of mucus (complex glycoprotein) that constitutes the inner, mucous layer of the tear film. The amount of mucin, as well as its proper hydration and character, is critical to the protection of the epithelia that it overlies. The amount of mucin is controlled by regulating the number of goblet cells, the rate of mucin secretion by the goblet cells, and the rate of mucin synthesis by the goblet cells.

SUMMARY

A method for increasing goblet cell density in epithelial tissue of a subject is disclosed herein. The method includes administering to the subject a therapeutically effective amount of an activator of CXCR3. In some embodiments, the epithelial tissue comprises conjunctival epithelium. In some embodiments, the subject has dry eye syndrome.

Further provided is a method of treating a subject having dry eye syndrome. The method includes selecting a subject having dry eye syndrome, and administering to the subject a therapeutically effective amount of an activator of CXCR3. In some cases, the subject has dry eye syndrome, or is at risk of developing dry eye syndrome due to mitomycin C (MMC) treatment during glaucoma surgery.

In some embodiments of the disclosed methods, the CXCR3 activator is an IP-10 protein or biologically active peptide fragment or variant thereof. In other embodiments, the CXCR3 activator is a PF4 protein or biologically active peptide fragment or variant thereof. In yet other embodiments, the CXCR3 activator is an IP-9 protein or biologically active peptide fragment or variant thereof. In some examples, the protein or peptide is modified to prevent the protein or peptide from crossing the blood-ocular barriers.

The foregoing and other objects, features, and advantages of the invention will become more apparent from the following detailed description, which proceeds with reference to the accompanying figures.

BRIEF DESCRIPTION OF THE DRAWINGS

FIG. 1: Histologic differences in treated blebs. Rabbit eyes were either untreated or treated with full length IP-10 (IP-10FL; SEQ ID NO: 12) or IP-10p (SEQ ID NO: 13). Treatment with either IP-10FL or IP-10p resulted in a reduction in inflammation and fibrosis, as indicated by the collagen content and elastic fiber thickness and orientation. The globes were embedded in paraffin and stained for hematoxylin and eosin (H&E) and Masson's trichrome. A semi-quantitative histological grading score was used to assess cellularity, collagen deposition (fibrosis) and inflammation between the four groups of animals.

(FIG. 2A) Quantitation of the number of capillaries, as determined by morphology, with a low-power field in the center of the injured area is shown in the graph. The data was derived from two independent experiments of at least three globes with each evaluated in three random low-power fields (shown are mean±SD, *$P<0.05$). (FIG. 2B) Representative images demonstrate the paucity of capillaries (arrows). Original magnifications ×100.

FIGS. 3A-3B: Decreased fibrosis in treated blebs. Histologic analysis of bleb tissue revealed reduced collagen deposition with IP-10FL or IP-10p treatment after injury. Collagen was quantified using Masson's trichrome staining. (FIG. 3A) METAMORPH™ analysis of the collagen confirmed that the IP-10FL- and IP-10p-treated animals had significantly less collagen compared to untreated animals. Images of untreated and IP-10-treated groups showed distinguishable patterns of collagen remodeling. (FIG. 3B) Representative images demonstrate the thickness of collagen (arrows). Original magnifications ×100.

FIGS. 4A-4B: Increased goblet cells in treated blebs. Tissue treated with IP-10FL or IP-10p exhibited an increase in the number of goblet cells. (FIG. 4A) Goblet cell number was calculated using the average cell number per high-powered field from six consecutive central bleb cross-sections of each specimen. (FIG. 4B) Representative images (Masson's trichrome stain) show the number of conjunctival goblet cells (asterisks).

(FIG. 5A) Goblet cells were evaluated in treated and untreated blebs. Bleb tissue was treated with MMC alone, IP-10p alone, or IP-10p as a perioperative "rescue" treatment at the time of MMC surgery. Bleb tissue treated with MMC alone exhibited a marked decrease in goblet cells. Bleb tissue treated with MMC and then IP-10p exhibited a rescue effect from MMC treatment alone and an increase in goblet cell density. (FIG. 5B) The images demonstrate an increase in conjunctival goblet cell density in MMC/IP-10p treatment versus MMC treatment alone.

SEQUENCE LISTING

Figure 2A:
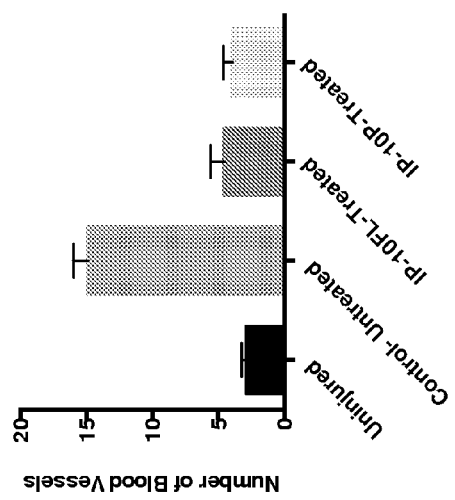
FIGS. 2A-2B: Arrested angiogenesis in treated blebs. Neovascularization in the bleb tissue was assessed using H&E staining.

The amino acid sequences listed in the accompanying sequence listing are shown using standard three letter code for amino acids, as defined in 37 C.F.R. 1.822. The Sequence Listing is submitted as an ASCII text file, created on Jul. 19, 1016, 6.66 KB, which is incorporated by reference herein. In the accompanying sequence listing:

SEQ ID NO: 1 is the amino acid sequence of human IP-10.

SEQ ID NO: 2 is the amino acid sequence of a human IP-10 fragment.

SEQ ID NO: 3 is the amino acid sequence of human PF4.

SEQ ID NO: 4 is the amino acid sequence of a human PF4 fragment.

SEQ ID NO: 5 is the amino acid sequence of a human IP-10 fragment.

SEQ ID NO: 6 is the amino acid sequence of a human IP-10 fragment/variant.

SEQ ID NO: 7 is the amino acid sequence of mouse IP-10.

SEQ ID NO: 8 is the amino acid sequence of a mouse IP-10 fragment.

SEQ ID NO: 9 is the amino acid sequence of a mouse IP-10 fragment.

SEQ ID NO: 10 is the amino acid sequence of a human PF4 fragment.

SEQ ID NO: 11 is the amino acid sequence of a human PF4 fragment.

SEQ ID NO: 12 is the amino acid sequence of a human IP-10 variant.

SEQ ID NO: 13 is the amino acid sequence of a human IP-10 fragment/variant.

SEQ ID NO: 14 is the amino acid sequence of human IP-9.

DETAILED DESCRIPTION

I. Abbreviations

CXCL C-X-C chemokine ligand
CXCR C-X-C chemokine receptor
IP-10 interferon-γ-inducible 10 kDa protein
IM intramuscular
IOP intraocular pressure
IV intravenous
MMC mitomycin C
PEG polyethylene glycol
PF4 platelet factor 4

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Activator of CXCR3: Refers to any type of compound, such as a protein, peptide, small molecule, nucleic acid molecule, organic compound or inorganic compound that promotes or enhances one or more functions or activities of CXCR3. In some embodiments, the CXCR3 activator is a protein ligand that binds CXCR3. In some examples, the CXCR3 activator is IP-10 or a biologically active fragment or variant thereof (such as a fragment or variant capable of preventing the loss of goblet cells). In other examples, the CXCR3 activator is PF4 or a biologically active fragment or variant thereof. In yet other examples, the activator is a CXCR3-specific antibody that activates CXCR3.

Administration: The introduction of a composition (such as a protein or peptide) into a subject by a chosen route. For example, if the chosen route is intravenous, the composition is administered by introducing the composition into a vein of the subject. Exemplary routes of administration include, but are not limited to, injection (such as intraocular, subcutaneous, intramuscular, intradermal, intraperitoneal, and intravenous), oral, intraductal, sublingual, transdermal, intranasal, topical, inhalation routes and via a medical implant.

Angiogenesis: The development of new blood vessels. Angiogenesis occurs normally following injury and is also observed in cancer where angiogenic factors establish the blood supply for malignant cells.

Aqueous humor: A transparent liquid contained in the anterior and posterior chambers of the eye.

Biologically active fragment or variant: Biologically active fragments (also referred to as biologically active peptides) or variants include any fragments or variants of a protein that retain an activity of the protein. In the context of the present disclosure, a biologically active fragment or variant of a protein (such as IP-10 or PF4) that binds CXCR3 is one that retains the ability to bind CXCR3 and/or retains the ability to prevent the loss of and/or reverse goblet cell loss, such as goblet cell loss in the eye. In some embodiments, the peptide variant comprises no more than 1, no more than 2, nor more than 3, no more than 4 or no more than 5 amino acid substitutions; such substitutions can be conservative or non-conservative substitutions.

Bleb: A protrusion from the surface of a cell or tissue, usually approximately hemispherical. A bleb may be fluid filled or supported by a meshwork of microfilaments. In ophthalmology, blebs may be formed intentionally in the treatment of glaucoma.

Blood-brain barrier: A separation of circulating blood and the brain extracellular fluid in the central nervous system. It occurs along all capillaries and consists of tight junctions around the capillaries that do not exist in normal circulation. Endothelial cells restrict the diffusion of microscopic objects (e.g. bacteria) and large or hydrophilic molecules into the cerebrospinal fluid, while allowing the diffusion of small hydrophobic molecules ($O_2$, hormones, $CO_2$). Cells of the barrier actively transport metabolic products such as glucose across the barrier with specific proteins. The eye spaces (the vitreous and aqueous humors) are considered on the CNS side of the barrier.

Blood-ocular barrier: The barrier created by endothelium of capillaries of the retina and iris, ciliary epithelium and retinal pigment epithelium. It is a physical barrier between the local blood vessels and most parts of the eye that prevents traversal of many substances.

Conjunctiva: The mucous membrane that lines the inner surface of the eyelid and the outer surface of the eye.

Conservative variants: "Conservative" amino acid substitutions are those substitutions that do not substantially affect or decrease an activity or antigenicity of a protein, such as IP-10 or an IP-10 peptide, or PF4 or a PF4 peptide. For example, IP-10 or PF4 (or a fragment thereof, such as any one of SEQ ID NOs: 2, 4-6 and 8-11) can include at most about 1, at most about 2, at most about 5, and most about 10, or at most about 15 conservative substitutions (such as 1, 2, 3, 4, 5, 6, 7, 8, 9, 10, 11, 12, 13, 14 or 15 conservative substitutions, such as 1 to 3, 1 to 5, 1 to 10, or 2 to 4 conservative substitutions, and retain biological activity, such as the ability to bind CXCR3 and/or inhibit goblet cell loss. In particular examples, IP-10 peptide variants and PF4 peptide variants have no more than 3 conservative amino acid substitutions. Specific, non-limiting examples of a conservative substitution include the following examples:

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variant also includes the use of a substituted amino acid in place of an unsubstituted parent amino acid. Non-conservative substitutions are those that reduce an activity or antigenicity.

CXCR3 (C-X-C chemokine receptor 3): A G protein-coupled receptor with selectivity for four chemokines, CXCL4/PF4 (platelet factor 4), CXCL9/Mig (monokine induced by interferon-γ), CXCL10/IP-10 (interferon-γ-inducible 10 kDa protein) and CXCL11/I-TAC (interferon-inducible T cell a-chemoattractant). Binding of chemokines to this protein induces cellular responses that are involved in leukocyte trafficking, most notably integrin activation, cytoskeletal changes and chemotactic migration. Alternatively spliced transcript variants encoding different isoforms have been found for this gene. One of the isoforms (CXCR3-B) shows high affinity binding to chemokine CXCL4/PF4.

Dextran: A complex, branched glucan (polysaccharide made of many glucose molecules) composed of chains of varying lengths (from 3 to 2000 kilodaltons).

Dry eye syndrome: A multifactorial disease of the tears and ocular surface that results in discomfort, visual disturbance, and tear film instability. Dry eye syndrome is generally caused by either decreased tear production or increased tear film evaporation. Dry eye syndrome is also known as keratoconjunctivitis sicca (KCS) or keratitis sicca. A number of different factors or conditions are associated with the development of dry eye syndrome, including age (eye dryness increases with age), gender (women are more likely to develop dry eye from hormonal changes associated with pregnancy, menopause or the use of oral contraceptives), use of medications that inhibit tear production, medical conditions associated with dry eyes and/or lacrimal gland dysfunction (e.g. rheumatoid arthritis, Sjögren's syndrome, Stevens-Johnson syndrome, Riley-Day syndrome, diabetes and thyroid disorders), environmental conditions that increase tear evaporation (e.g., exposure to smoke, wind and dry climates), corneal injury, infection, contact lens use and refractive eye surgery (such as LASIK). In the context of the present disclosure, dry eye syndrome can be caused by any one or any combination of disease, conditions or other factors.

Epithelium: Tissue composed of one or more layers that lines most internal and external surfaces of the body and its organs.

Fibrosis: The formation of excess fibrous connective tissue in an organ or tissue in a reparative or reactive process.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain to internal stop codons. For example, a fusion protein can include a CXCR3 activator (such as an IP-9, IP-10 or PF4 protein or peptide) fused to a heterologous protein.

Goblet cells: Glandular epithelial cells that secrete mucin. Goblet cells are found in the conjunctiva and in the epithelial lining of many organs, such as in the intestinal and respiratory tracts. Goblet cells are the primary source of tear mucus.

Heterologous: A heterologous protein or polypeptide refers to a protein or polypeptide derived from a different source or species.

Increasing goblet cell density: In the context of the present disclosure, "increasing goblet cell density" refers to increasing the number of goblet cells within in a particular tissue (or particular section of tissue), e.g. in the conjunctiva of a subject. Goblet cell density can increase, for example, by replenishing goblet cells that have been lost due to a particular disease or condition. Goblet cell density can also be increased by preventing the loss of goblet cells, such as the loss of goblet cells that would occur as the result of a medical condition in the absence of treatment.

Inert molecule: A molecule that will not chemically react with other substances under normal circumstances. In the context of the present disclosure, examples of large inert molecules include polyethylene glycol (PEG) and dextran.

IP-9: A member of the CXC chemokine superfamily. IP-9 is a ligand for CXCR3 and is capable of inducing chemotactic responses in activated T cells. IP-9 is also known as chemokine (C-X-C motif) ligand 11 (CXCL11). IP-10 sequences are publically available, such as through GENBANK™ (see, for example, Gene ID 6373 for human IP-9 sequences). An exemplary human IP-9 sequence is set forth herein as SEQ ID NO: 14.

IP-10 (interferon-γ-inducible 10 kDa protein): A chemokine of the CXC subfamily and ligand for the receptor CXCR3. Binding of this protein to CXCR3 results in pleiotropic effects, including stimulation of monocytes, natural killer and T-cell migration, modulation of adhesion molecule expression, and inhibition of vessel formation. IP-10 is also known as chemokine (C-X-C motif) ligand 10 (CXCL10). IP-10 sequences are publically available, such as through GENBANK™ (see, for example, Gene ID 3627 for human IP-10 sequences; see also GENBANK™ Accession No. P02778). Exemplary human and mouse IP-10 sequences are set forth herein as SEQ ID NO: 1 and SEQ ID NO: 7, respectively. Exemplary IP-10 peptide fragments and variants are set forth herein as SEQ ID NOs: 2, 5, 6, 8 and 9.

Isolated: An "isolated" biological component (such as a nucleic acid molecule, protein, or cell) has been substantially separated or purified away from other biological components in the cell or tissue of the organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins.

Mitomycin C (MMC): A type of aziridine-containing natural product isolated from *Streptomyces* species. In the treatment of glaucoma, mitomycin C is applied topically to prevent scarring during glaucoma filtering surgery.

Ophthalmic composition: A composition suitable for administration to the eye or ocular surface.

Peptide or polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide," "peptide," or "protein" as used herein are intended to encompass any amino acid sequence and include modified sequences such as glycoproteins. The terms "polypeptide" and "peptide" are specifically intended to cover naturally occurring proteins, as well as those which are recombinantly or synthetically produced.

In some embodiments, a polypeptide is between 10 and 600 amino acids in length, including 10 to 100, 10 to 50, or 10 to 30, amino acids in length. In particular examples, a CXCR3 activator is a IP-10 peptide of about 19 to about 23 amino acids, such as about 21 or 22 amino acids. In other specific examples, the CXCR3 activator is a PF4 peptide of about 27 to about 31 amino acids, such as about 29 amino acids. In other examples, the PF4 peptide is about 10 to about 20 amino acids, such as about 13 to about 18 amino acids, for example 13 amino acids or 18 amino acids. In other particular examples, a CXCR3 activator is an IP-9 peptide of about 18 to about 34 amino acids, such as about 22 to about 30 amino acids.

An "IP-10 polypeptide" or "IP-10 peptide" is a series of contiguous amino acid residues from an IP-10 protein. Similarly, a "PF4 polypeptide" or "PF4 peptide" is a series of contiguous amino acid residues from an IP-10 protein, and an "IP-9 polypeptide" or "IP-10 peptide" is a series of contiguous amino acid residues from an IP-9 protein. In some examples, the term further refers to variations of these peptides in which there are conservative substitutions of amino acids, so long as the variations do not alter by more than about 20% (such as no more than about 1%, about 5%, or about 10%) the ability of the peptide to bind CXCR3 and/or inhibit loss goblet cells.

A "residue" refers to an amino acid or amino acid mimetic incorporated in a polypeptide by an amide bond or amide bond mimetic.

PF4 (platelet factor 4): A small cytokine belonging to the CXC chemokine family. PF4 is a 70-amino acid protein that is released from the alpha-granules of activated platelets and binds with high affinity to heparin. Its major physiologic role appears to be neutralization of heparin-like molecules on the endothelial surface of blood vessels, thereby inhibiting local antithrombin III activity and promoting coagulation. As a strong chemoattractant for neutrophils and fibroblasts, PF4 is believed to play a role in inflammation and wound repair. PF4 is also known as CXCL4. PF4 is known to bind the B isoform of CXCR3 (CXCR3-B). Sequences for PF4 are publically available (see, for example, GENBANK™ Gene ID 5196). An exemplary human PF4 sequence is set forth herein as SEQ ID NO: 3. Exemplary PF4 peptide sequences are set forth herein as SEQ ID NOs: 4, 10 and 11.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition, 1975, describes compositions and formulations suitable for pharmaceutical delivery of the proteins herein disclosed. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. For topical application to the eye, agents can be mixed, for example, with artificial tears and other emulsions. See section V below for a description and pharmaceutical/ophthalmic compositions and administration thereof.

Polyethylene glycol (PEG): A polyether compound with many applications from industrial manufacturing to medicine. PEG has also been known as polyethylene oxide (PEO) or polyoxyethylene (POE), depending on its molecular weight, and under the trade name CARBOWAX™. PEG, PEO, or POE refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. PEG and PEO are liquids or low-melting solids, depending on their molecular weights. PEGs are prepared by polymerization of ethylene oxide and are commercially available over a wide range of molecular weights from 300 g/mol to 10,000,000 g/mol.

Preventing, treating or ameliorating a disease: "Preventing" a disease refers to inhibiting the full development of a disease. "Treating" refers to a therapeutic intervention that ameliorates a sign or symptom of a disease (such as dry eye syndrome) or pathological condition after it has begun to develop. "Ameliorating" refers to the reduction in the number or severity of signs or symptoms of a disease (e.g. dry eye).

Purified: The term "purified" does not require absolute purity; rather, it is intended as a relative term. Thus, for example, a purified peptide or protein, or other active compound is one that is isolated in whole or in part from naturally associated proteins and other contaminants. In certain embodiments, the term "substantially purified" refers to a peptide or protein, or other active compound that has been isolated from a cell, cell culture medium, or other crude preparation and subjected to fractionation to remove various components of the initial preparation, such as proteins, cellular debris, and other components.

Recombinant: A recombinant nucleic acid molecule or protein is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids and proteins that have been altered solely by addition, substitution, or deletion of a portion of the natural nucleic acid molecule or protein.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a particular polypeptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. In addition, Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a polypeptide are typically characterized by possession of at least about 75%, for example at least about 80%, 90%, 95%, 96%, 97%, 98% or 99% sequence identity counted over the full length alignment with the amino acid sequence of the polypeptide using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Subject: Living multi-cellular vertebrate organisms, a category that includes both human and veterinary subjects, including human and non-human mammals. In one example, a subject is one who has a dry eye syndrome.

Synthetic: Produced by artificial means in a laboratory, for example a synthetic protein or peptide can be chemically synthesized in a laboratory.

Therapeutically effective amount: A quantity of a specified agent (such as a CXCR3 activator) sufficient to achieve a desired effect in a subject, cell or culture being treated with that agent. In some embodiments, a therapeutically effective amount of a CXCR3 activator is an amount of CXCR3 activator that prevents or inhibits loss of goblet cells, such as loss of goblet cells in the eye. In some embodiments, a therapeutically effective amount of a CXCR3 activator is an amount sufficient to prevent or ameliorate one or more symptoms of a dry eye syndrome in a subject.

Trabeculectomy: A surgical procedure used in the treatment of glaucoma to relieve intraocular pressure by removing part of the eye's trabecular meshwork and adjacent structures. This procedure allows drainage of aqueous humor from within the eye to underneath the conjunctiva where it is absorbed.

Vitreous humor: A transparent, gel-like substance that fills the eyeball between the lens and the retina.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety; sequences associated with the disclosed GENBANK™ numbers and GENBANK™ Gene ID numbers are incorporated by reference for the sequences available on Jan. 17, 2014. In case of conflict, the present specification, including explanations of terms, will control. In addition, the materials, methods, and examples are illustrative only and not intended to be limiting.

III. Overview of Several Embodiments

Provided herein is a method for increasing goblet cell density in epithelial tissue of a subject. The method includes administering to the subject a therapeutically effective amount of an activator of CXCR3. In some embodiments, the epithelial tissue comprises conjunctival epithelium. In some examples, the subject suffers from dry eye syndrome. In some examples, the subject has undergone glaucoma surgery, such as trabeculectomy. In some cases, the subject has dry eye syndrome, or is at risk of developing dry eye syndrome, due to MMC treatment during glaucoma surgery.

Further provided is a method of treating a subject having dry eye syndrome. The method includes selecting a subject having dry eye syndrome, and administering to the subject a therapeutically effective amount of an activator of CXCR3. The dry eye syndrome can result from any one or a combination of diseases, conditions or disorders that lead to symptoms of dry eye. For example, dry eye may be the result of increased age, hormonal changes, the use of medications that inhibit tear production, medical conditions associated with dry eyes and/or lacrimal gland dysfunction such as keratoconjunctivitis sicca, exposure to environmental conditions that increase tear evaporation, the use of contact lenses or ophthalmic surgery, such as refractive eye surgery or a surgery for the treatment of glaucoma. In some examples, the subject has rheumatoid arthritis, Sjögren's syndrome, diabetes or a thyroid disorder. In other examples, the subject has previously had refractive eye surgery, or has cicatricial changes that cause exposure of the cornea, as in cicatricial entropion. In other examples, the subject has undergone surgery for glaucoma, such as trabeculectomy.

The mode of administration of the CXCR3 activator will vary depending upon, for example, the type of compound to be administered (such as a protein or peptide), the disease or disorder to be treated, and the stage or severity of the disease. In some embodiments, the CXCR3 activator is administered topically, by injection (such as by subconjunctival injection) or by medical implant.

In some examples, the CXCR3 activator is administered topically in a cream or eye drop to allow for adsorption into the eye.

In other examples, the CXCR3 activator is administered by injection into the vitreous humor or the aqueous humor. The method can include a single injection of the CXCR3 activator, or multiple injections as needed, such as 2, 3, 4 or 5 injections.

In other examples, the CXCR3 activator is impregnated in a medical implant, is coated on the surface of a medical implant, or both.

In some embodiments, the activator of CXCR3 comprises a protein or peptide that binds CXCR3.

In some embodiments, the protein that binds CXCR3 comprises IP-10, or a biologically active fragment or variant thereof, such as an IP-10 peptide. In some embodiments, the IP-10 is human IP-10 of SEQ ID NO: 1, mouse IP-10 of SEQ ID NO: 7, or a variant human IP-10 of SEQ ID NO: 12. In some examples, the IP-10 protein is at least 80%, at least 85%, at least 90%, at least 95%, at least 96%, at least 97%, at least 98% or at least 99% identical to SEQ ID NO: 1, SEQ ID NO: 7 or SEQ ID NO: 12. In specific non-limiting examples, the amino acid sequence of the IP-10 protein comprises or consists of SEQ ID NO: 1, SEQ ID NO: 7 or SEQ ID NO: 12. In other embodiments, the protein that binds CXCR3 is PF4 (such as human PF4), or a biologically active fragment or variant thereof, such as a PF4 peptide. In some examples, the PF4 protein is at least 80%, at least 85%, at least 90%, at least 95%, at least 96%, at least 97%, at least 98% or at least 99% identical to SEQ ID NO: 3. In specific non-limiting examples, the amino acid sequence of the PF4 protein comprises or consists of SEQ ID NO: 3. In yet other embodiments, the protein that binds CXCR3 is IP-9 (such as human IP-9), or a biologically active fragment or variant thereof, such as a IP-9 peptide. In some examples, the IP-9 protein is at least 80%, at least 85%, at least 90%, at least 95%, at least 96%, at least 97%, at least 98% or at least 99% identical to SEQ ID NO: 14. In specific non-limiting examples, the amino acid sequence of the IP-9 protein comprises or consists of SEQ ID NO: 14.

The biologically active fragment or variant of IP-10, PF4 or IP-9 can be any fragment or variant that retains the capacity to activate CXCR3 and/or increase goblet cell density. In some embodiments, the biologically active fragment of IP-10 is a fragment comprising or consisting of amino acid residues 77-98 or residues 78-98 of SEQ ID NO: 1. In some examples, the biologically active fragment of IP-10 comprises an amino acid sequence at least 80%, at least 85%, at least 90%, at least 95%, at least 96%, at least 97%, at least 98% or at least 99% identical to SEQ ID NO: 2, SEQ ID NO: 5, SEQ ID NO: 6, SEQ ID NO: 8, SEQ ID NO: 9, or SEQ ID NO: 13. In some examples, the biologically active fragment of IP-10 comprises an amino acid sequence at least 80%, at least 90%, at least 95%, at least 96%, at least 97%, at least 98% or at least 99% identical to SEQ ID NO: 2, SEQ ID NO: 5, SEQ ID NO: 6, SEQ ID NO: 8, SEQ ID NO: 9 or SEQ ID NO: 13, wherein the fragment is no more than 40 amino acids, such as a fragment 15 to 40, 20 to 40, 20 to 30, 20 to 25, or 21 to 23 amino acids in length. In some examples, the biologically active fragment of IP-10 consists of SEQ ID NO: 2, SEQ ID NO: 5, SEQ ID NO: 6, SEQ ID NO: 8, SEQ ID NO: 9 or SEQ ID NO: 13 and includes no more than 10 conservative amino acid substitutions, such as 1 to 10 or 1 to 5 or 1 to 3 conservative amino acid substitutions. In specific non-limiting examples, the amino acid sequence of the IP-10 fragment comprises or consists of SEQ ID NO: 2, SEQ ID NO: 5, SEQ ID NO: 6, SEQ ID NO: 8, SEQ ID NO: 9 or SEQ ID NO: 13.

In other embodiments, the biologically active fragment of PF4 is a fragment comprising or consisting of amino acid residues 7-35, residues 58-70 or residues 53-70 of SEQ ID NO: 3. In some examples, the biologically active fragment of PF4 comprises an amino acid sequence at least 80%, at least 85%, at least 90%, at least 95%, at least 96%, at least 97%, at least 98% or at least 99% identical to SEQ ID NO: 4, SEQ ID NO: 10 or SEQ ID NO: 11. In some examples, the biologically active fragment of PF4 comprises an amino acid sequence at least 80%, at least 90%, at least 95%, at least 96%, at least 97%, at least 98% or at least 99% identical to SEQ ID NO: 4, SEQ ID NO: 10 or SEQ ID NO: 11, wherein the fragment is no more than 40 amino acids, such as a fragment 15 to 40, 20 to 40, 25 to 35, 27 to 31, 28 to 30, or about 29 amino acids in length. In some examples, the biologically active fragment of PF4 consists of SEQ ID NO: 4, SEQ ID NO: 10 or SEQ ID NO: 11 and includes no more than 10 conservative amino acid substitutions, such as 1 to 10 or 1 to 5 or 1 to 3 conservative amino acid substitutions. In specific non-limiting examples, the amino acid sequence of the PF4 fragment comprises or consists of SEQ ID NO: 4, SEQ ID NO: 10 or SEQ ID NO: 11.

In some embodiments, the protein or peptide is modified to prevent the protein or peptide from crossing the blood-ocular barrier when administered to the subject. The protein or peptide can be, for example, modified to increase hydrophobicity or to increase overall charge of the protein or peptide. In particular embodiments, modification comprises conjugation of the protein or peptide to a heterologous molecule, such as a large inert molecule. In some examples, the modification comprises conjugation of the protein or peptide to polyethylene glycol (PEG) or dextran (see, for example, Mehvar, "Dextrans for targeted and sustained delivery of therapeutic and imaging agents," *J Control Release* 69(1):1-25, 2000).

The therapeutically effective amount of the agents administered can vary depending upon the desired effects, the subject to be treated and the type of agent administered. In one example, the method includes administration of at least 1 µg of a therapeutic agent to the subject (such as a human subject). For example, a human can be administered at least at least 0.01 µg, at least 0.1 µg, at least 1 µg or at least 1 mg of the agent as a single dose, or in multiple doses (such as daily doses), such as 10 μg to 100 μg per dose, 100 μg to 1000 μg per dose, for example 10 μg per dose, 100 μg per dose, or 1000 μg per dose. In some examples, the subject is administered at least 1 μg (such as 1-100 μg) intravenously of the protein or peptide (such as a composition that includes any one of SEQ ID NOs: 1-14 or a variant thereof). In one non-limiting example, a subject is administered about 10 μg of the CXCR3 activator (such as an IL-10, PF4 or IP-9 protein or peptide). In another non-limiting example, a subject is administered about 100 μg of the CXCR3 activator (such as an IL-10, PF4 or IP-9 protein or peptide).

The dosage can be administered in divided doses (such as 2, 3, or 4 divided doses per day or over multiple days), or in a single dosage daily. In particular examples, the subject is administered the therapeutic composition on a multiple daily dosing schedule, such as at least two consecutive days, 10 consecutive days, and so forth, for example for a period of weeks, months, or years. In one example, the subject is administered the therapeutic composition daily for a period of at least 30 days, such as at least 2 months, at least 4 months, at least 6 months, at least 12 months, at least 24 months, or at least 36 months. In another example, the subject is administered about 3, about 4, about 5, about 5 or about 7 doses per week. In one example, the subject is administered a dose on days 1, 2, 4 and 7.

The compositions, such as those that include an IP-10, PF4 or IP-9 protein or peptide, can further include one or more biologically active or inactive compounds (or both), such as other agents known in the art for reducing or treating one or more signs or symptoms associated with dry eye syndrome and conventional non-toxic pharmaceutically acceptable carriers, respectively. For example, additional therapeutic agents that enhance the therapeutic effect of the disclosed compositions are included.

IV. IP-10, PF4 and IP-9 Proteins and Fragments and Variants Thereof

In some embodiments, the present disclosure contemplates the use of an IP-10 protein, or a biologically active peptide fragment or variant thereof, as an activator of CXCR3, such as to increase the density of goblet cells and/or treat dry eye syndrome. Sequences for IP-10 proteins from a variety of different species are known in the art and are publically accessible, such as through the GENBANK™ database. For example, IP-10 sequences are known for at least the following species: human (see GENBANK™ Gene ID 3627), mouse (Gene ID 15945), rat (Gene ID 24592), pig (Gene ID 494019), chimpanzee (Gene ID 461242), dog (Gene ID 478432), cow (Gene ID 615107), macaque (Gene ID 574243), horse (Gene ID 100050993) and sheep (Gene ID 44297).

In some embodiments of the methods disclosed herein, the IP-10 protein is human IP-10, or a biologically active fragment or variant thereof. Exemplary IP-10 protein and peptide sequences are provided below.

Human IP-10 (full-length; GENBANK ™ Accession No. P02778):
(SEQ ID NO: 1)
MNQTAILICCLIFLTLSGIQGVPLSRTVRCTCISISNQPVNPRSLEKLE
IIPASQFCPRVEIIATMKKKGEKRCLNPESKAIKNLLKAVSKERSKRSP Human IP-10 variant (IP-10FL):
(SEQ ID NO: 12)
VPLSRTVRCTCISISNQPVNPRSLEKLEIIPASQFSPRVEIIATMKKKG
EKRCLNPESKAIKNLLKAVSKEMSKRSP Human IP-10 peptide fragments/variants:
(SEQ ID NO: 2)
ESKAIKNLLKAVSKERSKRSP (SEQ ID NO: 5)
PESKAIKNLLKAVSKERSKRSP (SEQ ID NO: 6)
ESKAIKNLLKAVSKEMSKRSP (IP-10p; SEQ ID NO: 13)
PESKAIKNLLKAVSKEMSKRSP Mouse IP-10 (full-length):
(SEQ ID NO: 7)
MNPSAAVIFCLILLGLSGTQGIPLARTVRCNCIHIDDGPVRMRAIGKLE
IIPASLSCPRVEIIATMKKNDEQRCLNPESKTIKNLMKAFSQKRSKRAP Mouse IP-10 fragments:
(SEQ ID NO: 8)
ESKTIKNLMKAFSQKRSKRAP (SEQ ID NO: 9)
PESKTIKNLMKAFSQKRSKRAP In some embodiments of the methods, the IP-10 protein is at least 85%, at least 90%, at least 95%, at least 96%, at least 97%, at least 98 or at least 99% identical to SEQ ID NO: 1, SEQ ID NO: 7 or SEQ ID NO: 12. In some embodiments, the IP-10 peptide is at least 85%, at least 90%, at least 95%, at least 96%, at least 97%, at least 98 or at least 99% identical to SEQ ID NO: 2, SEQ ID NO: 5, SEQ ID NO: 6, SEQ ID NO: 8, SEQ ID NO: 9 or SEQ ID NO: 13. In some examples, the IP-10 peptide is no more than 40 amino acids in length, such as a biologically active fragment of IP-10 that is 15 to 40, 20 to 40, 20 to 30, 20 to 25, or 21 to 23 amino acids in length.

In other embodiments, the present disclosure contemplates the use of a PF4 protein, or a biologically active peptide fragment thereof, as an activator of CXCR3, such as to increase the density of goblet cells and/or treat dry eye syndrome. Sequences for PF4 proteins from a variety of different species are known in the art and are publically accessible, such as through the GENBANK™ database. For example, PF4 sequences are known for at least the following species: human (see GENBANK™ Gene ID 5196), mouse (Gene ID 56744), rat (Gene ID 360918), chimpanzee (Gene ID 740477), cow (Gene ID 507790) and macaque (Gene ID 703451).

In some embodiments of the methods disclosed herein, the PF4 protein is human PF4, or a biologically active fragment thereof. Exemplary PF4 protein and peptide sequences are provided below.

Human PF4 protein (full-length):
(SEQ ID NO: 3)
EAEEDGDLQCLCVKTTSQVRPRHITSLEVIKAGPHCPTAQLIATLKNGR
KICLDLQAPLYKKIIKKLLES Human PF4 peptides:
(SEQ ID NO: 4)
DLQCLCVKTTSQVRPRHITSLEVIKAGPH -continued

PLYKKIIKKLLES (SEQ ID NO: 10)

LDLQAPLYKKIIKKLLES (SEQ ID NO: 11)

In some embodiments of the methods, the PF4 protein is at least 85%, at least 90%, at least 95%, at least 96%, at least 97%, at least 98 or at least 99% identical to SEQ ID NO: 3. In some embodiments, the PF4 peptide is at least 85%, at least 90%, at least 95%, at least 96%, at least 97%, at least 98 or at least 99% identical to SEQ ID NO: 4, SEQ ID NO: 10 or SEQ ID NO: 11. In some examples, the PF4 peptide is no more than 40 amino acids in length, such as a biologically active fragment of PF4 that is 10 to 40, 10 to 30, 15 to 40, 20 to 40, 20 to 30, 25 to 35, 10 to 20, 13 to 18, or 27 to 31 amino acids in length.

In other embodiments, the present disclosure contemplates the use of an IP-9 protein, or a biologically active peptide fragment thereof, as an activator of CXCR3, such as to increase the density of goblet cells and/or treat dry eye syndrome. Sequences for IP-9 proteins from a variety of different species are known in the art and are publically accessible, such as through the GENBANK™ database. For example, IP-9 sequences are known for at least the following species: human (see GENBANK™ Gene ID 6373), mouse (Gene ID 56066), rat (Gene ID 305236), chimpanzee (Gene ID 739195), cow (Gene ID 516104), pig (Gene ID 100169744) and macaque (Gene ID 574372).

In some embodiments of the methods disclosed herein, the IP-9 protein is human IP-9.

Human IP-9 protein (full length):
(SEQ ID NO: 14)
MSVKGMAIALAVILCATVVQGFPMFKRGRCLCIGPGVKAVKVADIEKAS
IMYPSNNCDKIEVIITLKENKGQRCLNPKSKQARLIIKKVERKNF In some embodiments of the methods, the IP-9 protein is at least 85%, at least 90%, at least 95%, at least 96%, at least 97%, at least 98 or at least 99% identical to SEQ ID NO: 14.

V. Ophthalmic Compositions and Administration Thereof

Methods of increasing goblet cell density in epithelial tissue of a subject are provided. In some embodiments, the method includes increasing goblet cell density in the conjunctiva of the subject by administering a suitable composition, such as an ophthalmic composition, topically, by injection (such as by subconjunctival injection) or by medical implant. The mode of administration of the CXCR3 activator, and the type of composition administered, will vary depending upon, for example, the type of compound to be administered (such as a protein or peptide), the disease or disorder to be treated, and the stage or severity of the disease.

In some examples, the CXCR3 activator is administered topically in a cream or eye drop to allow for adsorption into the eye. In other examples, the CXCR3 activator is administered by injection into the vitreous humor or the aqueous humor, or into the wall of the eye, for example, subconjuctivally. The method can include a single injection of the CXCR3 activator, or multiple injections as needed, such as 2, 3, 4 or 5 injections. In yet other examples, the CXCR3 activator is impregnated in a medical implant, is coated on the surface of a medical implant, or both.

In other embodiments, topical administration of a composition comprising a CXCR3 activator, such as an ophthalmic composition, is carried out by instillation of the composition, or by topical administration from a device, such as a pump-catheter system, a selective release device, or a contact lens. The preparation for topical administration can include dispersion of the preparation in a carrier vehicle, such as a liquid, gel, ointment, or liposome. In some embodiments, the carrier vehicle is non-naturally occurring.

Any ophthalmic device that resides on the eye can be used as a carrier for a composition comprising a CXCR3 activator. These devices can provide optical correction, wound care, drug delivery, diagnostic functionality, cosmetic enhancement or effect, or any combination thereof. The term "lens" includes, but is not limited to, soft contact lenses, hard contact lenses, overlay lenses, and optical inserts. Suitable contact lens can be made from any of a wide family of known materials including, but not limited to, commercially available hydrogel formulations such as etafilcon, polymacon, vifilcon, genfilcon A, lenefilcon A, galyfilcon, senofilcon, omafilcon, balafilcon, lotrafilcon A, lotrafilcon B, comfilcon and the like. The compositions can be incorporated into or onto a contact lens by any suitable method, such as by soaking, coating, grafting, non-covalent association and/or imprinting.

In some embodiments, the composition comprising a CXCR3 activator is administered to the eye of a subject as a drop or within an ointment, gel, or liposome. In some examples, the compounds are infused or instilled into the tear film via a pump-catheter system. In other examples, the compounds are contained within continuous or other selective-release devices, for example, membranes. As a further example, the compounds are attached to or carried by and/or contained within contact lenses that are placed on the eye. In yet other examples, the composition is contained within a liquid spray that is applied to the ocular surface.

In some embodiments, a topical preparation is made by combining a composition comprising a CXCR3 activator with an appropriate carrier and/or preservative. In some examples, the carrier or preservative is non-naturally occurring. The preparation can also contain a physiologically compatible vehicle. In some examples, the vehicles is water, a buffered aqueous solution, a polyether (such as polyethylene glycol), a polyvinyl (such as polyvinyl alcohol), a cellulose derivative (such as methylcellulose or hydroxypropyl methylcellulose), a petroleum derivative (such as mineral oil or white petrolatum), animal fat (such as lanolin), vegetable fat (such as peanut oil), a polymers of acrylic acid (such as carboxypolymethylene gel), a polysaccharide (such as dextran), a glycosaminoglycan (such as sodium hyaluronate), or a salt (such as sodium chloride or potassium chloride).

In some embodiments, the vehicle is any water-based solution that is useful for the packaging or storing of contact lenses. Typical solutions include, without limitation, saline solutions, other buffered solutions, and deionized water. Suitable saline solutions include salts including, without limitation, sodium chloride, sodium borate, sodium phosphate, sodium hydrogenphosphate, sodium dihydrogenphosphate, or the corresponding potassium salts of the same. These ingredients are generally combined to form buffered solutions that include an acid and its conjugate base, so that addition of acids and bases cause only a relatively small change in pH. The buffered solutions may additionally include 2-(N-morpholino)ethanesulfonic acid (MES), sodium hydroxide, 2,2-bis(hydroxymethyl)-2,2',2"-nitrilotriethanol, n-tris(hydroxymethyl)methyl-2-aminoethanesulfonic acid, citric acid, sodium citrate, sodium carbonate, sodium bicarbonate, acetic acid, sodium acetate, ethylenediamine tetraacetic acid, and combinations thereof. In some examples, the solution is a borate buffered or phosphate buffered saline solution.

In some embodiments, the compositions comprising a CXCR3 activator are pharmaceutical or ophthalmic composition. Pharmaceutical compositions and ophthalmic compositions are formulated according to the mode of administration to be used. Compositions can include, for example, additives for isotonicity, which can include sodium chloride, dextrose, mannitol, sorbitol and lactose. In some cases, isotonic solutions such as phosphate or borate buffered saline are used. Stabilizers include gelatin and albumin. Alternatively, the compositions may be dispersed to form an emulsion, such a liposome or double emulsions. The compositions and/or preparations can be sterile and pyrogen free. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21$^{st}$ Edition (2005).

For ophthalmic application, ophthalmic compositions can be prepared using a physiological saline solution as a major vehicle. Ophthalmic solutions can be maintained at a comfortable pH with an appropriate buffer system. The formulations may also contain conventional, pharmaceutically acceptable preservatives, stabilizers and surfactants.

In some embodiments, the ophthalmic compositions include demulcents or film forming materials. In some examples, the demulcents are non-naturally occurring. Examples of demulcents include, but are not limited to, polymers such as polyvinyl alcohol, povidone, hydroxypropyl methyl cellulose, poloxamers, carboxymethyl cellulose, hydroxyethyl cellulose, acrylates; surfactants such as polyoxyethylene (80) sorbitan monooleate and glycerin.

In some embodiments, the ophthalmic compositions include a buffer. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed.

In some embodiments, the ophthalmic compositions include a preservative. The preservative may vary, and may include any compound or substance suitable for preventing microbial contamination in an ophthalmic liquid subject to multiple uses from the same container. In some examples, the preservative is non-naturally occurring. Preservatives that may be used in the pharmaceutical compositions disclosed herein include, but are not limited to, cationic preservatives such as quaternary ammonium compounds including benzalkonium chloride, polyquad, and the like; guanidine-based preservatives including polyhexamethylene biguanide (PHMB), chlorhexidine, and the like; chlorobutanol; mercury preservatives such as thimerosal, phenylmercuric acetate and phenylmercuric nitrate; and oxidizing preservatives such as stabilized oxychloro complexes.

In some embodiments, the ophthalmic compositions include a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. In some examples, the surfactant is non-naturally occurring.

Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated arylphenols; ethoxylated fatty acids; ethoxylated fatty esters or oils (animal and vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives.

In some embodiments, the ophthalmic compositions include a stabilizer. In some examples, the stabilizer is non-naturally occurring. Examples of suitable stabilizers include, but are not limited to, polyvinyl alcohol, povidone, hydroxypropyl methyl cellulose, poloxamers, carboxymethyl cellulose, hydroxyethyl cellulose, and acrylates such as acrylates/C10-30 alkyl acrylate crosspolymer.

In some embodiments, the ophthalmic compositions include a tonicity agent. The tonicity agent may vary, and may include any compound or substance useful for adjusting the tonicity of an ophthalmic liquid. Examples include, but are not limited to, salts, particularly sodium chloride, potassium chloride, mannitol and glycerin, or any other suitable ophthalmically acceptable tonicity adjustor. The amount of tonicity agent may vary depending upon whether an isotonic, hypertonic, or hypotonic liquid is desired.

In some embodiments, the ophthalmic compositions include an antioxidant. The antioxidant may vary, and may include any compound or substance that is useful in reducing oxidation of any compound present in an ophthalmically acceptable liquid. Examples, include but are not limited to, sodium metabisulfite, sodium thiosulfate, acetylcysteine, butylated hydroxyanisole, and butylated hydroxytoluene.

In some embodiments, the ophthalmic compositions include a chelating agent. The chelating agent may vary, and may include any compound or substance that is capable of chelating a metal. In one examples, the chelating agent is edetate disodium, although other chelating agents may also be used in place or in conjunction with it.

Compositions may be aqueous solutions or emulsions, or some other acceptable liquid form. For an emulsion, one or more oils may be used to form the emulsion. Suitable oils include, but are not limited to anise oil, castor oil, clove oil, cassia oil, cinnamon oil, almond oil, corn oil, arachis oil, cottonseed oil, safflower oil, maize oil, linseed oil, rapeseed oil, soybean oil, olive oil, caraway oil, rosemary oil, peanut oil, peppermint oil, sunflower oil, eucalyptus oil, sesame oil, and the like.

The disclosed methods include administering a CXCR3 activator in a single dose or in multiple doses. The compositions can be administered either as individual therapeutic agents or in combination with other therapeutic agents, such as with other agents for the treatment of dry eye syndrome. Compositions comprising a CXCR3 activator can be combined with conventional therapies, which can be administered sequentially or simultaneously.

The following examples are provided to illustrate certain particular features and/or embodiments. These examples should not be construed to limit the disclosure to the particular features or embodiments described.

EXAMPLES

Example 1: Treatment with IP-10 Increases Goblet Cell Density in the Conjunctiva This example describes the finding that treatment of injured blebs following trabeculectomy reduces inflammation and fibrosis, arrests angiogenesis and increases the number of goblet cells in the conjunctiva.

In the following studies, modified trabeculectomy was performed in New Zealand white rabbits using a 22 gauge angiocatheter inserted into the anterior chamber. Rabbit eyes were either untreated or treated with IP-10FL (SEQ ID NO: 12) or IP-10p (SEQ ID NO: 13) by intraoperative topical application. Untreated and injured bleb formation was confirmed and assessed weekly after the procedure. All animals were euthanized at the end of the six week study.

To evaluate histological differences in treated and untreated blebs, the globes were embedded in paraffin and stained with hematoxylin and eosin (H&E) and Masson's trichrome. A-semi quantitative histological grading score was used to assess cellularity, collagen deposition (fibrosis) and inflammation to compare findings between the four animal groups (uninjured, control (injured), IP-10 full length treated and IP-10p treated). Treatment with either IP-10 full length or IP-10p led to a reduction in inflammation and fibrosis indicated by the collagen content and elastic fiber thickness and orientation (FIG. 1).

Figure 2B:
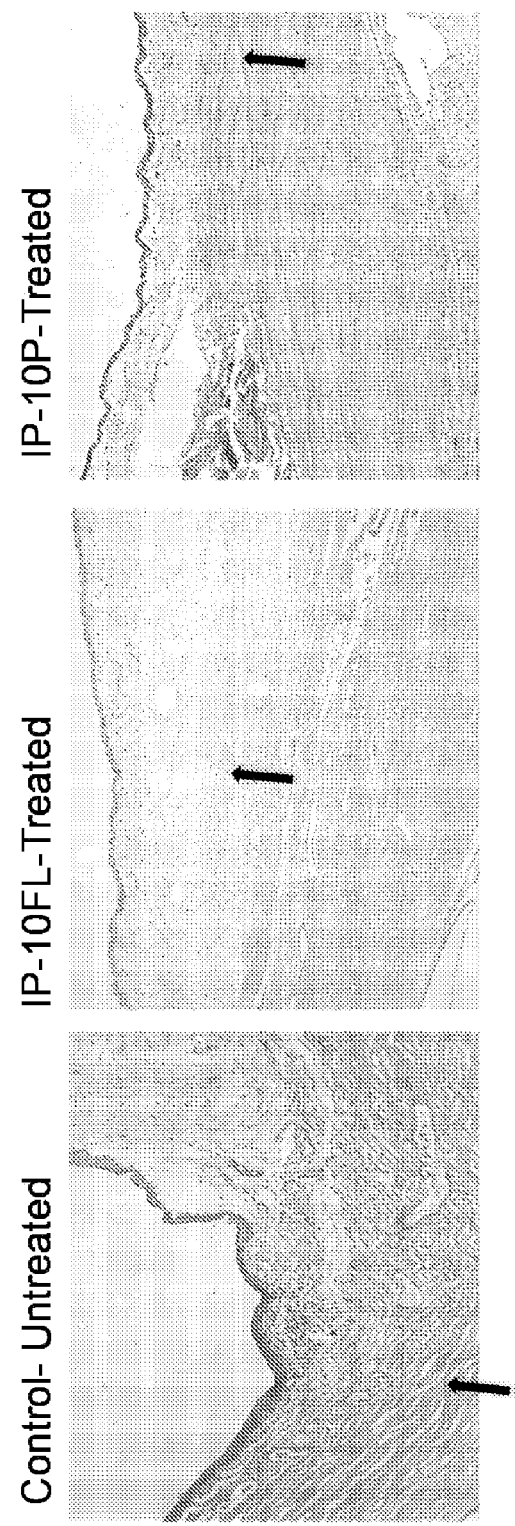

Next, angiogenesis was evaluated in treated and untreated blebs. Neovascularization in the bleb tissue was assessed by H&E staining. As shown in FIG. 2A and FIG. 2B, treatment with IP-10FL or IP10p significantly reduced the number of capillaries present in blebs.

In addition, histologic analysis of bleb tissue revealed reduced collagen deposition following treatment with IP-10FL or IP-10p after injury. Collagen was quantified using Masson's trichrome staining. METAMORPH™ analysis of the collagen confirmed that the IP-10FL- and IP-10p-treated tissue had significantly less collagen compared to untreated tissue (FIG. 3A). Images of untreated and IP-10-treated groups showed distinguishable patterns of collagen remodeling (FIG. 3B).

Goblet cells were also evaluated in treated and untreated blebs. Bleb tissue treated with IP-10FL or IP-10p exhibited an increase in the number of goblet cells (FIG. 4A). The images shown in FIG. 4B demonstrate an increase in conjunctival goblet cell density in both treatment groups.

Example 2: Increase in Goblet Cell Density Following Treatment with IP-10p and MMC This example describes the finding that treatment of injured blebs with a combination of mitomycin C (MMC) and IP-10 peptide increases the density of goblets cells, compared to treatment with MMC alone.

Figure 5A:
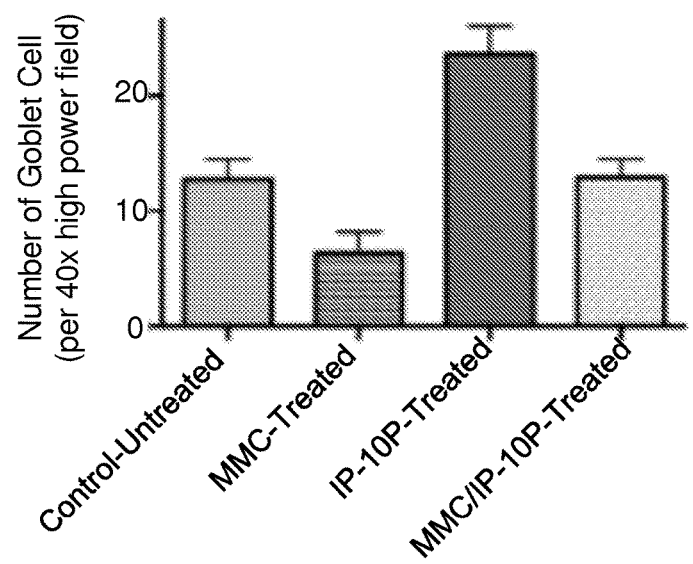
FIGS. 5A-5B: Goblet cells in treated and untreated blebs.
Figure 5B:
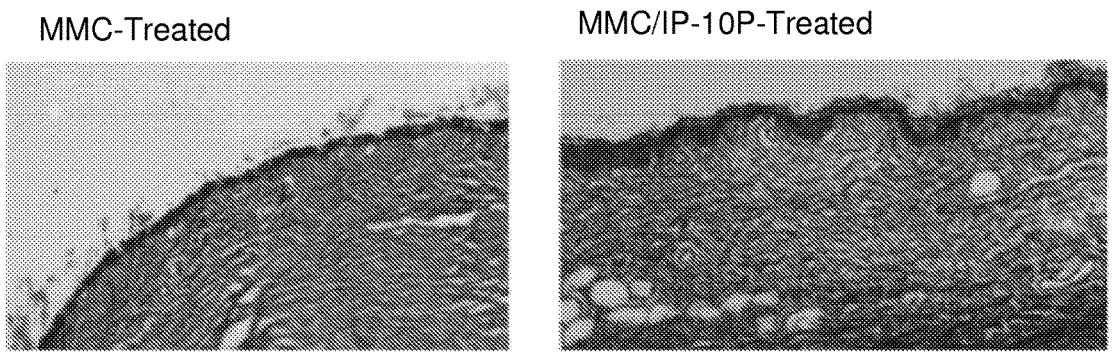

Modified trabeculectomy was performed in New Zealand white rabbits using a 22 gauge angiocatheter inserted into the anterior chamber. Bleb tissue was treated with MMC alone, IP-10p (SEQ ID NO: 13) alone, or IP-10p as a perioperative rescue treatment at the time of MMC surgery. As shown in FIG. 5A, bleb tissue treated with MMC alone exhibited a marked decrease in goblet cells. Bleb tissue treated with MMC and then IP-10p exhibited a rescue effect from MMC treatment alone and an increase in goblet cell density. The images shown in FIG. 5B demonstrate an increase in conjunctival goblet cell density in MMC/IP-10p treatment versus MMC treatment alone.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

---

The invention claimed is:

1. A method for increasing goblet cell density in epithelial tissue of a subject who has dry eye syndrome, comprising administering to the subject a therapeutically effective amount of an activator of CXCR3, wherein the activator of CXCR3 is an isolated peptide that binds CXCR3 and comprises an amino acid sequence consisting of SEQ ID NO: 2, 5, 12, or 13, thereby increasing goblet cell density in the subject.

2. The method of claim 1, wherein the epithelial tissue comprises conjunctival epithelium.

3. The method of claim 1, further comprising selecting a subject having dry eye syndrome, and administering to the subject a therapeutically effective amount of an activator of CXCR3, thereby treating dry eye syndrome in the subject.

4. The method of claim 1, wherein the activator of CXCR3 is administered topically, by injection or by medical implant.

5. The method of claim 4, wherein:
the activator of CXCR3 is administered topically in a cream or eye drop;
the activator of CXCR3 is administered by injection into the vitreous humor or the aqueous humor; or
the activator of CXCR3 is impregnated in the medical implant, is coated on the surface of the medical implant, or both.

6. The method of claim 1, wherein the peptide is modified to prevent the peptide from crossing the blood-ocular barrier when administered to the subject.

7. The method of claim 6, wherein the modification comprises conjugation of the peptide to a large inert molecule, to polyethylene glycol (PEG) or to dextran.

8. The method of claim 1, wherein the therapeutically effective amount of the activator of CXCR3 is about 1 µg to about 1 mg, or about 10 µg to about 100 µg.

9. The method of claim 8, wherein the therapeutically effective amount is about 100 µg.

10. The method of claim 1, wherein the activator of CXCR3 is present in a pharmaceutically acceptable carrier suitable for administration to the eye.

11. The method of claim 2, wherein the subject has undergone glaucoma surgery.

12. The method of claim 11, wherein the glaucoma surgery comprises trabeculectomy.

13. The method of claim 1, wherein the subject developed or is at risk for dry eye syndrome due to the use of MMC during glaucoma surgery.

14. A method for treating a subject who has, or is at risk of developing dry eye syndrome, comprising administering to the subject a therapeutically effective amount of an activator of CXCR3, wherein the activator of CXCR3 is an isolated peptide that binds CXCR3 and comprises an amino acid sequence consisting of SEQ ID NO: 2, 5, 12, or 13.

15. The method of claim 14, further comprising selecting a subject who has or is at risk of developing dry eye syndrome.

16. The method of claim 14, wherein the activator of CXCR3 is administered topically, by injection or by medical implant.

17. The method of claim 14, wherein:
the activator of CXCR3 is administered topically in a cream or eye drop;
the activator of CXCR3 is administered by injection into the vitreous humor or the aqueous humor; or
the activator of CXCR3 is impregnated in the medical implant, is coated on the surface of the medical implant, or both.

18. The method of 14, wherein the peptide is modified to prevent the peptide from crossing the blood-ocular barrier when administered to the subject.

19. The method of claim 18, wherein the modification comprises conjugation of the peptide to a large inert molecule, to polyethylene glycol (PEG) or to dextran.

20. The method of claim 14, wherein the therapeutically effective amount of the activator of CXCR3 is about 1 µg to about 1 mg, or about 10 µg to about 100 µg.

* * * * *

UNITED STATES PATENT AND TRADEMARK OFFICE
CERTIFICATE OF CORRECTION

PATENT NO. : 9,895,419 B2
APPLICATION NO. : 15/113035
DATED : February 20, 2018
INVENTOR(S) : Yates-Binder et al.

Page 1 of 1

It is certified that error appears in the above-identified patent and that said Letters Patent is hereby corrected as shown below:

In the Specification

Column 6, Line 22, "contain to internal" should read --contain internal--

Column 6, Line 36, "within in a" should read --within a--

Column 16, Line 42, "vehicles is" should read --vehicle is--

Signed and Sealed this
Eighteenth Day of December, 2018

Andrei Iancu
*Director of the United States Patent and Trademark Office*